US008916513B2

(12) United States Patent
Anderson (10) Patent No.: US 8,916,513 B2
(45) Date of Patent: Dec. 23, 2014

(54) DIOXIRANE COMPOUNDS AND USES THEREOF

(75) Inventor: Kraig Anderson, Burlingame, CA (US)

(73) Assignee: Empire Technology Development LLC, Wilmington, DE (US)

( * ) Notice: Subject to any disclaimer, the term of this patent is extended or adjusted under 35 U.S.C. 154(b) by 236 days.

(21) Appl. No.: 13/554,633

(22) Filed: Jul. 20, 2012

(65) Prior Publication Data

US 2014/0187467 A1    Jul. 3, 2014

(51) Int. Cl.

| | | |
|---|---|---|
| C07D 317/02 | (2006.01) | |
| C07D 321/00 | (2006.01) | |
| C07D 491/113 | (2006.01) | |
| C11D 3/30 | (2006.01) | |
| C11D 3/20 | (2006.01) | |
| C11D 7/32 | (2006.01) | |
| C11D 7/26 | (2006.01) | |
| C11D 3/28 | (2006.01) | |

(52) U.S. Cl.
CPC .......... *C07D 321/00* (2013.01); *C07D 491/113* (2013.01); *C11D 3/30* (2013.01); *C11D 3/2096* (2013.01); *C11D 7/3281* (2013.01); *C11D 7/3209* (2013.01); *C11D 7/267* (2013.01); *C11D 3/28* (2013.01)
USPC ........... 510/499; 510/500; 510/504; 510/505; 549/200

(58) Field of Classification Search
CPC .......... C11D 3/2096; C11D 3/28; C11D 3/30; C11D 7/267; C11D 7/3209; C11D 7/3281; C07D 321/00
USPC ................... 510/499, 500, 504, 505; 549/200
See application file for complete search history.

(56) References Cited

U.S. PATENT DOCUMENTS

| 5,525,121 | A | 6/1996 | Heffner et al. | |
|---|---|---|---|---|
| 7,465,411 | B2 | 12/2008 | Martin | |
| 7,582,594 | B2 | 9/2009 | Delcomyn et al. | |
| 2002/0122775 | A1* | 9/2002 | Reinhardt et al. | 424/49 |
| 2007/0219108 | A1 | 9/2007 | Martin | |

FOREIGN PATENT DOCUMENTS

| EP | 1288283 | * | 3/2003 |
|---|---|---|---|
| WO | WO-2011/005630 | | 1/2011 |

OTHER PUBLICATIONS

Adam et al., "Dioxiranes—A New class of Powerful Oxidants," Acc. Chem. Res., 1989, vol. 22, pp. 205-211.
Curci et al., "Dioxirane oxidations—Taming the reactivity-selectivity principle," Pure & Appl. Chem., 1995, vol. 67, No. 5, pp. 811-822.
Deary et al., "Evidence for cyclodextrin dioxiranes," Carbohydrate Research, 1998, vol. 309, pp. 17-29.
Deary et al., "Evidence for cyclodextrin dioxiranes. Part 2. Catalytic and enantioselective properties of cyclodextrin dioxiranes formed from keto-derivatised hydroxypropyl-cyclodextrins," Carbohydrate Research, 1999, vol. 317, pp. 10-18.
Du et al., "Investigation of Physicochemical Properties of Lactam-Based Bronsted Acidic Ionic Liquids," J. Phys. Chem. B, 2005, vol. 109, No. 41, pp. 19542-19546.
International Search Report and Written Opinion for Intl. Pat. Appln. No. PCT/US2012/025211, mailed on Apr. 17, 2012, 9 pp.
JLA Limited, OTEX product description, 2011, webpage: http://www.jla.com/otex, accessed on Jun. 13, 2012.
Murray et al., "Chemistry of Dioxiranes. 4. Oxygen Atom Insertion into Carbon-Hydrogen bonds by Dimethyldioxirane," J. Am. Chem. Soc., 1986, vol. 108, pp. 2470-2472.
Murray et al., "Dioxiranes—Synthesis and Reactions of Methyldioxiranes," J. Org. Chem., 1985, vol. 50, pp. 2847-2853.
Russo, A. et al., "Difluorodioxirane," Angewandte Chemie international Edition in English, 1993, vol. 32, pp. 905-907.
Sawwan, N. et al., "Generation of mono- and bis-dioxiranes from 2,3-butanedione," Journal of Organic Chemistry, 2006, vol. 71, No. 15, pp. 5796-5799.
Singh et al., "Chemistry of Dioxiranes. 21. Thermal Reactions of Dioxiranes," J. Org. Chem., 1992, vol. 57, pp. 4263-4270.
Sung, K., "Substituent effects on stability of oxiranes, oxirenes, and dioxiranes," Can. J. Chem., 2000, vol. 78, 562-567.
Wallace et al., "Use of In Situ-Generated Dimethyldioxirane for Inactivation of Biological Agents," Environ. Sci. Technol., 2005, vol. 39, pp. 6288-6292.
Wilk, K.A. et al,. "Synthesis and hydrolysis of chemodegradable cationic surfactants containing the 1,3-dioxolane moiety," Journal of the American Oil Chemists' Society Jan. 1994, vol. 71, Issue 1, pp. 81-85.
Wong et al., "Dioxiranes Generated in Situ from Pyruvates and Oxone as Environmentally Friendly Oxidizing Agents for Disinfection," Environ. Sci. Technol., 2006, vol. 40, No. 2, pp. 625-630.

* cited by examiner

*Primary Examiner* — Gregory R Delcotto
(74) *Attorney, Agent, or Firm* — Foley & Lardner LLP (57) ABSTRACT

A dioxirane-containing compound has a first substituent that is an alkyl, polyalkoxy, aryl, heteroaryl, or heterocyclyl group, and a second substituent that is an electron withdrawing group, and where the first and second substituents can optionally join to form a cycloalkyl or heterocyclyl group. The dioxirane-containing compound can be used as an oxidant, surfactant, and/or an ionic liquid.

18 Claims, 1 Drawing Sheet

DIOXIRANE COMPOUNDS AND USES THEREOF

CROSS-REFERENCE TO RELATED APPLICATIONS

This application claims the benefit of International Application Serial No. PCT/US2012/025211, filed on Feb. 15, 2012, the entire disclosure of which is hereby incorporated by reference for all purposes in its entirety as if fully set forth herein.

FIELD

The present technology relates to dioxirane-containing compounds and uses of such compounds in consumer or industrial applications related to cleaning, disinfection, and decontamination, as oxidants, chiral oxidants, surfactants, ionic liquids, and combinations thereof.

BACKGROUND

The following description is provided to assist the understanding of the reader. None of the information provided or references cited is admitted to be prior art to the present technology.

A wide variety of oxidants are employed for bleaching, cleaning, disinfection, and decontamination, yet they suffer from various drawbacks. Some oxidants are harsh, such as the hypochlorites used in household bleach. Other oxidants, such as hydrogen peroxide, are ineffective at low (i.e., safe) concentrations. Still other oxidants, such as ozone, can be difficult to control at low concentrations, or they can generate undesirable byproducts, such as chlorinated organics from the use of hypochlorites.

A particularly strong class of oxidants, the peroxymonosulfate (POMS) salts, such as Oxone®, suffer from the above-indicated drawbacks, but can be reacted with ketones to create the relatively selective dioxirane oxidants. Dioxiranes react with a variety of organic substrates, e.g., by inserting oxygen atoms into carbon-carbon double bonds, which provides a bleaching action and makes the oxidized substrate more water-soluble and susceptible to rinsing. Despite these practical attributes, dioxiranes have found limited success as agents for cleaning, disinfection, and decontamination. However, such dioxiranes, especially those which are volatile, may be inconvenient or incompatible for use with typical hot water washing processes. For example, dimethyl dioxirane and its corresponding ketone, acetone, are readily volatilized under typical hot water washing conditions, which may lead to undesirable volatile organic emissions, flammable vapors, difficulty ensuring sufficient concentrations of dimethyl dioxirane for the desired oxidations, or the like. Moreover, high concentrations of volatile dioxiranes, which are effectively cyclic peroxides, are undesirable. As such, dioxiranes such as dimethyl dioxirane have not found practical use for consumer or industrial applications related to cleaning, disinfection, and decontamination.

Therefore, there is a need for new dioxirane oxidants which are safer, more selective, and more effective under conditions such as those required of consumer or industrial applications related to cleaning, disinfection, and decontamination.

SUMMARY

The present technology provides for dioxirane oxidants which are strong, stable, safe, selective, and effective under a broad range of conditions. This is achieved by configuring the dioxirane compounds to include substituents that render the compound an effective surfactant and/or an ionic liquid. Compared to conventional oxidants, including known dioxiranes, the present dioxirane oxidants are easier to control and do not generate undesirable byproducts such as chlorinated organics. The present technology provides a dioxirane compounds, compositions including such dioxirane compounds, and methods of making and using such dioxirane compounds.

The present technology provides a dioxirane oxidant (Scheme 1) that includes a dioxirane moiety stabilized by an electron withdrawing group (EWG), bonded to a solvating group (SG), thus forming a surfactant and/or an ionic solvent. The SG and EWG are optionally joined [----] as shown. The dioxirane is readily generated (and regenerated) from a ketone precursor by reaction with peroxymonosulfate (POMS). In certain embodiments, surfactant dioxiranes (e.g., where the EWG is ionic or non-ionic, the SG is relatively large and hydrophobic, e.g., $C_4$-$C_{24}$ alkyl) provide highly effective oxidants, e.g., for hydrophobic contaminants in washwater. In other embodiments, the surfactant properties of these compounds concentrate the dioxirane at the contaminants, even though the average dioxirane concentration in the washwater can remain quite low. In certain embodiments, ionic liquid dioxiranes (e.g., where the EWG is ionic, the SG is relatively small, e.g., $C_1$-$C_6$ alkyl) have relatively low vapor pressures and large liquid ranges.

Scheme 1

Further, both the surfactant and ionic liquid dioxiranes are optionally configured as chiral oxidants by selecting a chiral SG or EWG. Their specificity makes them useful in selective chemical oxidations. The new compounds are useful for bleaching, cleaning, disinfection and decontamination.

In one aspect, a compound represented by Formula I, or a salt thereof, is provided:

I

In the above Formula I, $R^1$ may be an alkyl, alkoxy, polyalkoxy, aryl, heteroaryl, or heterocyclyl group; $R^2$ is an electron withdrawing group; and $R^1$ and $R^2$ can optionally join to form a cycloalkyl or heterocyclyl group; provided that if $R^2$ is $CF_3$, $CF_2Cl$, or $CO_2R^A$; then $R^1$ is not $CH_3$ or $CF_3$; where $R^A$ is H, $CH_3$, $CH_2CH_2CH_3$, $CH(CH_3)_2$, or $CH_2$-β-cyclodextrin.

In another aspect, a compound represented by Formula II, or salt thereof, is provided:

II

In the above Formula II, $R^3$ may be an electron withdrawing group and n is 1, 2 or 3.

In yet another aspect, a composition is provided where the composition includes water, a peroxymonosulfate salt, and one or more compounds or salts thereof represented by Formula III:

III

In the above Formula III, $R^1$ is an alkyl, alkoxy, polyalkoxy, aryl, heteroaryl, or heterocyclyl group; $R^2$ is an electron withdrawing group; and $R^1$ and $R^2$ can optionally join to form a cycloalkyl or heterocyclyl group; provided that if $R^2$ is $CF_3$, $CF_2Cl$, or $CO_2R^4$; then $R^1$ is not $CH_3$ or $CF_3$; where $R^4$ is H, $CH_3$, $CH_2CH_2CH_3$, $CH(CH_3)_2$, or $CH_2$-β-cyclodextrin.

In still another aspect, a process is provided where the process includes contacting a compound represented by Formula III with a peroxymonosulfate salt to form a compound represented by Formula I:

III

I

In the above Formula I and Formula III, $R^1$ is an alkyl, alkoxy, polyalkoxy, aryl, heteroaryl, or heterocyclyl group; $R^2$ is an electron withdrawing group; and $R^1$ and $R^2$ can optionally join to form a cycloalkyl or heterocyclyl group; provided that if $R^2$ is $CF_3$, $CF_2Cl$, or $CO_2R^4$; then $R^1$ is not $CH_3$ or $CF_3$; where $R^4$ is H, $CH_3$, $CH_2CH_2CH_3$, $CH(CH_3)_2$, or $CH_2$-β-cyclodextrin.

In another aspect a method of cleaning an article is provided where the method includes the step of contacting the article with a compound or composition of any of the above aspects. In yet another aspect is provided a method of bleaching an article including the step of contacting the article with a compound or composition of any of the above aspects. In a further aspect is provided a method of disinfecting an article including the step of contacting the article with a compound or composition of any of the above aspects. In another aspect is provided a method of decontaminating an article including the step of contacting the article with a compound or composition of any of the above aspects. In yet another aspect is provided a method of oxidizing a substrate including the step of contacting the substrate with a compound or composition of any of the above aspects.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth below and throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups.

As used herein, "polyalkoxy" groups include two or more alkyl groups, as previously defined, where the two or more alkyl groups are each linked together by an oxygen atom. Polyalkoxy groups include alkyl groups having straight chain, branched chain, or cyclic alkyl moieties having 1 to 12 carbons, where the two or more alkyl groups are each linked together by an oxygen atom. In some embodiments, each alkyl group of the polyalkoxy group has from 2 to 6 carbon atoms, from 2 to 4 carbons, 3 carbons, or 2 carbon atoms. Exemplary polyalkoxy groups include polyethyleneoxide and polypropyleneoxide groups.

Cycloalkyl groups are cyclic alkyl groups having from 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and polycyclic ring systems. Monocyclic groups include, e.g., cyclopropyl, cyclobutyl, cyclopentyl, cyclohexyl, and cycloheptyl groups. Bicyclic and polycyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted alkenyl groups may be mono-substituted or substituted more than once, such as, but not limited to, mono-, di- or tri-substituted with substituents such as those listed above. Representative substituted alkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Aryl groups are cyclic aromatic hydrocarbons that do not contain heteroatoms. Thus aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, and naphthenyl groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups.
Representative substituted aryl groups may be mono-substituted or substituted more than once, such as, but not limited to, 2-, 3-, 4-, 5-,
or
6-substituted phenyl or naphthyl groups, which may be substituted with groups including, but not limited to, amino, alkoxy, alkyl, cyano, and/or halo. In some embodiments, aryl is phenyl or naphthyl. In certain embodiments, aryl is phenyl.

Heteroaryl groups include an aromatic ring containing, for example, 5 to 12, or 5 to 10 atoms including one or more heteroatoms (e.g., 1, 2, 3 or 4 heteroatoms) selected from N, O and S and with the remaining ring atoms being carbon. Heteroaryl groups do not contain adjacent S and O atoms. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. Heteroaryl groups may be monocyclic or polycyclic (e.g., bicyclic, tricyclic). In some embodiments, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine. In some embodiments, more than one ring of a polycyclic heteroaryl group are aromatic. Examples include indole, isoindole, indazole, benzoimidazole, benzotriazole, benzofuran, and benzoxazole.

The terms "alkylene," "alkenylene," and "arylene," alone or as part of another substituent, means a divalent radical derived from an alkyl, cycloalkyl, alkenyl, aryl, or heteroaryl group, respectively, as exemplified by —CH$_2$CH$_2$CH$_2$CH$_2$—. For alkylene, alkenyl, or aryl linking groups, no orientation of the linking group is implied.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —NH$_2$, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C(O)—), a carbonate linkage (—O—C(O)O—), a carbamate linkage (—O—C(O)NH— or —O—C(O)NR—), and the like.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynylene, arylene, hetero moieties. Additionally, the substituents may be pendent from, or integral to, the carbon chain itself.

As used herein, an "electron withdrawing group," (EWG), refers to any chemical group that draws electrons from the atom or functional group to which it is attached. In some embodiments, the electron withdrawing group is independently selected from —N$^+$R$^4$R$^5$R$^6$, NO$_2$, CN, C(O)R$^7$, CO$_2$R$^7$SOR$^7$, SO$_2$R$^7$, CONR$^7$R$^7$, PO$_3$R$^7$R$^7$, aryl, heteroaryl, or alkyl substituted with NO$_2$, CN, C(O)R$^7$, CO$_2$R$^7$SOR$^7$, SO$_2$R$^7$, or one or more halogens, wherein R$^4$ is H or alkyl; R$^5$ is H or alkyl, R$^6$ is H or alkyl, and any two of R$^4$, R$^5$, and R$^6$ can optionally join to form a heterocyclyl group, and each R$^7$ may independently be H, alkyl, polyalkoxy, aryl, heteroaryl, or a heterocyclyl group.

As used herein, an "solvating group," (SG), refers to any chemical group that is relatively hydrophobic, e.g., straight chain, branched chain, or cyclic C$_4$-C$_{24}$ alkyl groups or straight chain, branched chain, or cyclic C$_4$-C$_{24}$ alkenyl groups.

Cyclodextrins, sometimes called cycloamyloses, are a family of compounds made up of sugar molecules bound together in a ring (i.e., cyclic oligosaccharides). Cyclodextrins are generally produced from starch by means of enzymatic conversion, and typically have five or more α-D-glucopyranoside units linked 1→4, as in amylose, a fragment of starch. Typical cyclodextrins contain six to eight glucose monomers arranged in a ring, and creating a cone shape. Exemplary cyclodextrins include α-cyclodextrin, having a six membered sugar ring molecule; β-cyclodextrin, having a seven sugar ring molecule; and γ-cyclodextrin, having an eight sugar ring molecule.

As noted, the present technology provides for dioxirane oxidants which are strong, stable, safe, selective, and effective under a broad range of conditions. In certain embodiments, this is achieved by configuring the dioxirane compounds to include substituents that render the compound an effective surfactant and/or an ionic liquid. Although the dioxirane moiety of the dioxirane compound is a highly reactive group, the substituents of the dioxirane compound impart useful characteristics (e.g., hydrophobicity, greater molecular weight) to make practical use of the dioxirane compound. The structure of the present oxidants makes them easier to control than conventional oxidants, including known dioxiranes, without the generation of undesirable byproducts, such as chlorinated organics.

The present technology provides dioxirane compounds, compositions including such dioxirane compounds, and methods of making and using such dioxirane compounds. The dioxirane compound is an oxidant that is generally reactive towards compounds and microorganisms, for use in applications that require an oxidant and/or a surfactant.

In one aspect, a compound represented by Formula I, or a salt thereof, is provided:

I

In Formula I, $R^1$ may be an alkyl, alkoxy, polyalkoxy, aryl, heteroaryl, or heterocyclyl group; $R^2$ is an electron withdrawing group; and $R^1$ and $R^2$ can optionally join to form a cycloalkyl or heterocyclyl group. However, in Formula I, when $R^2$ is $CF_3$, $CF_2Cl$, or $CO_2R^4$; then $R^1$ is not $CH_3$ or $CF_3$. Where $R^2$ is $CO_2R^4$, $R^4$ may be H, $CH_3$, $CH_2CH_2CH_3$, $CH(CH_3)_2$, or $CH_2$-β-cyclodextrin.

In any of the above embodiments, $R^1$ may be a $C_4$-$C_{24}$ alkyl. For example, $R^1$ may be a $C_8$-$C_{16}$ alkyl. In any of the above embodiments, $R^1$, $R^2$, both $R^1$ and $R^2$, or $R^1$ and $R^2$ when optionally joined to form a cycloalkyl or heterocyclyl group may include a chiral center. By introducing chirality into the group, selective oxidations may be achieved. A chiral center is a functional group that lacks mirror symmetry. For example, any carbon atom in $R^1$ or $R^2$ with four different substituents lacks mirror symmetry and may impart chirality to the group. Suitable chiral groups for $R^1$ include but-2-yl, 3-methylbutan-2-yl, pent-2-yl, 3-methylpentan-2-yl, 3-propylpentan-2-yl, 4-methylpentan-2-yl, 2-methyl-3-oxapentyl, hex-2-yl, 2-methylhexan-2-yl, 2-ethylhexan-2-yl, 3-methylhexan-2-yl, 4-methylhexan-2-yl, 2-methyl-3-oxahexyl, heptan-2-yl, octan-2-yl, 1,1,1-trifluorooctan-2-yl, nonan-2-yl, decan-2-yl, dodecan-2-yl, 1-methoxyprop-2-yloxy, 1-propoxyprop-2-yloxy, 1-butoxyprop-2-yloxy, but-2-yloxy, 1-ethoxyprop-2-yloxy, 3-methylbutan-2-yloxy, pent-2-yloxy, 3-methylpentan-2-yloxy, 3-oxy-4-methylpent-2-yl, 3-propylpentan-2-yloxy, 4-methylpentan-2-yloxy, hex-2-yloxy, 2-methylhexan-2-yloxy, 2-ethylhexan-2-yloxy, 3-methylhexan-2-yloxy, 4-methylhexan-2-yloxy, heptan-2-yloxy, octan-2-yloxy, 6-methoxyoctan-2-yloxy, 2-fluorooct-2-yloxy, 2-fluoromethyloctan-2-yloxy, 1,1,1-trifluorooctan-2-yloxy, nonan-2-yloxy, decan-2-yloxy, dodecan-2-yloxy, and 2-fluorodec-2-yloxy, or the like.

According to some embodiments, $R^2$ is $-N^+R^4R^5R^6$, $NO_2$, CN, $C(O)R^7$, $CO_2R^7SOR^7$, $SO_2R^7$, aryl, heteroaryl, or alkyl substituted with $NO_2$, CN, $C(O)R^7$, $CO_2R^7SOR^7$, $SO_2R^7$, or one or more halogens; $R^4$ is H or alkyl; $R^5$ is H or alkyl; $R^6$ is H or alkyl; and any two of $R^4$, $R^5$, and $R^6$ can optionally join to form a heterocyclyl group. Where $R^2$ is an alkyl group that is substituted as described, the substitution is typically on the carbon atom that is α- or β- to the carbon atom with the dioxirane moiety, otherwise electronic effects of the electron withdrawing group are minimized. In such compounds, $R^7$ may be H, alkyl, polyalkoxy, aryl, heteroaryl, or a heterocyclyl group. In one embodiment, $R^2$ is $-N^+R^4R^5R^6$. In other embodiments, $R^4$, $R^5$, and $R^6$ are the same and are H or $C_1$-$C_{12}$ alkyl. In other embodiments, at least two of $R^4$, $R^5$, and $R^6$ are the same and are H or $C_1$-$C_{12}$ alkyl. In yet other embodiments, $R^4$, $R^5$, and $R^6$ are all different, and are H or $C_1$-$C_{12}$ alkyl, resulting in the central N atom being chiral. In other embodiments, $R^4$, $R^5$, and $R^6$ are independently H, methyl, or benzyl.

According to another aspect, a compound represented by Formula II, or a salt thereof, is provided:

II

In Formula II, $R^3$ is an electron withdrawing group and n is 1, 2 or 3. In other embodiments, n is 1. In certain embodiments, $R^3$ is perhaloalkylene, $-N^+R^4R^5-$, $-SO-$, or $-SO_2-$. $R^4$ may then be H or alkyl; $R^5$ may be H or alkyl; or $R^4$ and $R^5$ can optionally join to form a heterocyclyl group with the nitrogen to which they are attached. In one embodiment, $R^3$ is $-N^+R^4R^5-$. In certain embodiments, $R^4$ and $R^5$ are the same and are H or $C_1$-$C_{12}$ alkyl. In other embodiments, $R^4$ and $R^5$ are different, and are H or $C_1$-$C_{12}$ alkyl. In certain embodiments, $R^4$ is $C_1$-$C_6$ alkyl. In other embodiments, $R^5$ is $C_1$-$C_6$ alkyl. In certain embodiments, $R^4$ and $R^5$ are independently selected from methyl, ethyl, propyl, or butyl. In certain embodiments, the $-N^+R^4R^5-$ is chiral at the nitrogen atom. In other embodiments, $R^4$ and $R^5$ are independently H, methyl, or benzyl. In certain embodiments, the compound represented by Formula II is an ionic liquid.

As noted above, the dioxirane compounds may be surfactant materials. Surfactants are materials that lower the surface tension of liquid. They are materials that can effectively cross interfacial barriers such as between a liquid and solid or between two liquids. Many surfactants are longer molecules having a hydrophilic end and a hydrophobic end. The hydrophilic end having an affinity for hydrophilic materials and the hydrophobic end having an affinity for hydrophobic materials.

Figure 1:
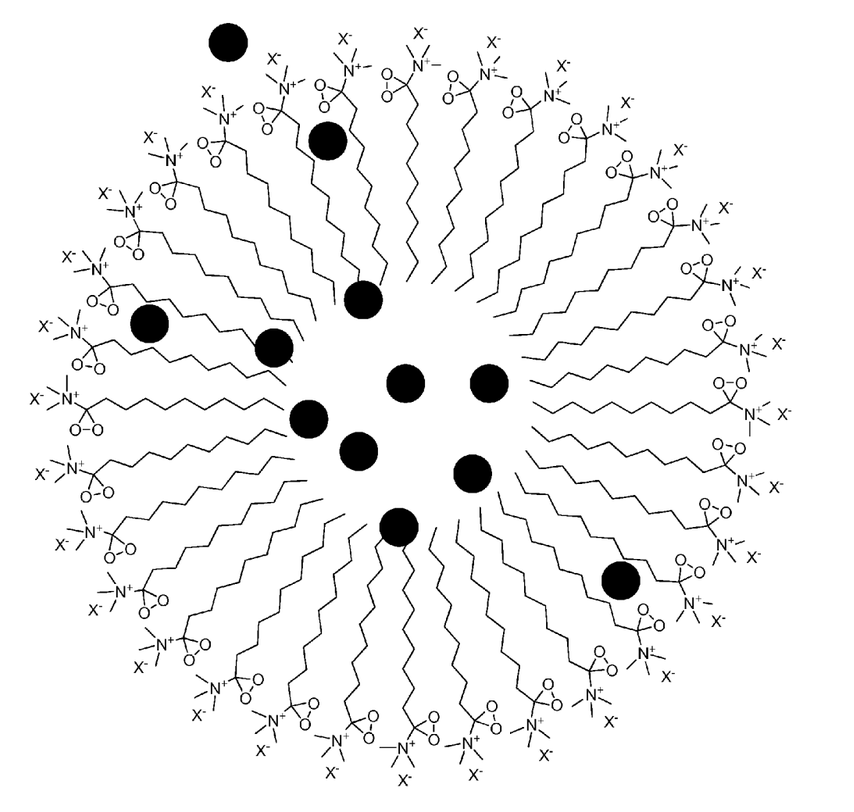
FIG. 1 illustrates a dioxirane surfactant, according to one embodiment.

In the above dioxirane compounds, the substituent alkyl groups tend to be hydrophobic, while the more polar or ionic groups such as, but not limited to, the $NO_2$, CN, $C(O)R^7$, $CO_2R^7SOR^7$, $SO_2R^7$, $-N^+R^4R^5R^6$ or $-N^+R^4R^5-$ groups tend to be hydrophilic. When such surfactant materials are placed in water, they may form micellular structures in the water with the hydrophilic groups in different molecules being associated with one another and the hydrophobic groups of different molecules being associated with one another. Thus, although dioxirane of the above compounds is in the region of the hydrophilic part of the compound, it may be put into close proximity with a hydrophobic substrate such that the hydrophobic substrate is oxidized. Thus, the surfactant dioxiranes can oxidize hydrophobic substances, where their polar structure may otherwise not have been effective. One example of a micelle of a dioxirane surfactant is illustrated in FIG. 1. FIG. 1 shows an illustration of such a micelle and how solvated substrates (dark circles) associate with the micelle, yet are able to contact the dioxirane functional group in order to be oxidized. The dynamic structure of micelles (or reverse micelles—the same compound in an oil or other hydrophobic substance would cause the hydrophobic groups to be on the outer sphere of the micelle) provides contact between the dioxirane and micelle-solvated substrates.

In another aspect, a composition is provided where the composition includes water, a peroxymonosulfate salt, and one or more compounds or salts thereof represented by Formula III:

III

In Formula III, $R^1$ is an alkyl, alkoxy, polyalkoxy, aryl, heteroaryl, or heterocyclyl group; $R^2$ is an electron withdrawing group; and $R^1$ and $R^2$ can optionally join to form a cycloalkyl or heterocyclyl group. However, if $R^2$ is $CF_3$, $CF_2Cl$, or $CO_2R^4$; then $R^1$ is not $CH_3$ or $CF_3$. Where $R^2$ is a group of formula $CO_2R^4$, then $R^4$ is H, $CH_3$, $CH_2CH_2CH_3$, $CH(CH_3)_2$, or $CH_2$-β-cyclodextrin. In the composition, the concentration of the compound represented by Formula III may be from about 1 ppm to about 10,000 ppm.

In yet another aspect, a composition is provided where the composition includes water, a peroxymonosulfate salt, and one or more compounds, or salts thereof, represented by Formula IV:

IV

In Formula IV, $R^3$ is perhaloalkylene, $-N^+R^4R^5-$, $-C(O)-$, $-SO-$, or $-SO_2-$; $R^4$ is H or alkyl; $R^5$ is H or alkyl; $R^4$ and $R^5$ can optionally join to form a heterocyclyl group; and n is 1, 2 or 3. In the composition, the concentration of the compound represented by Formula IV may be about 1 ppm to about 10,000 ppm.

Where included, the peroxymonosulfate salt may include those such as, but not limited to, lithium peroxymonosulfate, sodium peroxymonosulfate, potassium peroxymonosulfate, tetramethylammonium peroxymonosulfate, tetraethylammonium peroxymonosulfate, trimethylammonium peroxymonosulfate, triethylammonium peroxymonosulfate, triisopropylammonium peroxymonosulfate, tetraisopropylammonium peroxymonosulfate, or benzyltriphenylphosphonium peroxymonosulfate. A combination of any two or more different peroxymonosulfates may also be used. In certain embodiments, the composition further includes at least one buffer. A buffer, as used herein, is a compound or mixture of compounds in aqueous solution that modulate or maintain pH of the aqueous solution when contacted with acid or base. Examples of buffers include: HCl, sodium citrate (pH 1-5); citric acid, sodium citrate (pH 2.5-5.6); acetic acid, sodium acetate (pH 3.7-5.6); $K_2HPO_4$, $KH_2PO_4$ (pH 5.8-8); $Na_2HPO_4$, $NaH_2PO_4$ (pH 6-7.5); $Na_2HPO_4$, citric acid (pH 3-8); N-cyclohexyl-2-aminoethanesulfonic acid (pH 8.6-10); borax, sodium hydroxide (pH 9.2-11); citric acid, potassium dihydrogen phosphate, boric acid, and diethyl barbituric acid (pH 2.6 to 12). Other examples of buffers may include McIlvaine's buffer, Carmody buffer, Britton-Robinson buffer, sulfamic acid/triethanolamine, citric acid/triethanolamine, tartaric acid/triethanolamine, succinic acid/triethanolamine, acetic acid/triethanolamine, 3-{[tris(hydroxymethyl)methyl]amino}propanesulfonic acid, N,N-bis(2-hydroxyethyl)glycine, tris(hydroxymethyl)methylamine, N-tris(hydroxymethyl)methylglycine, 3-[N-Tris(hydroxymethyl)methylamino]-2-hydroxypropanesulfonic acid, 4-2-hydroxyethyl-1-piperazineethanesulfonic acid, 2-{[tris(hydroxymethyl)methyl]amino}ethanesulfonic acid, 3-(N-morpholino)propanesulfonic acid, piperazine-N,N'-bis(2-ethanesulfonic acid), and 2-(N-morpholino)ethanesulfonic acid.

Any of the above composition may also include suitable, organic solvent. For example such organic solvents may include, but are not limited to, acetonitrile, tert-butanol, propylene carbonate, propylene glycol, or polypropylene glycol. Combinations of any two or more such solvents may also be used.

Any of the above compositions may further include added surfactants. Suitable surfactants include, but are not limited to, tetrabutylammonium hydrogen sulfate (TBAHS), cetyltrimethylammonium (CTMA) chloride, or octyl phenol ethoxylate. Combinations of any two or more such surfactants may also be used.

Any of the above compositions may further include one or more of a detergent, an oxidant, a disinfectant, or a bleach catalyst. Representative detergents include, but are not limited to, for example, solid and liquid detergents for use in consumer cleaning products or in large-scale industrial cleaning applications (e.g., dish washing, laundry washing, etc.). Suitable solid detergents include, but are not limited to, any powder or granulate as well as solid block-like material which may be produced by pressing a powder, by casting, or even by extrusion or other manufacturing methods. Solid detergents also include semi-solid material like a gel with high viscosity which will not flow from the solid detergent reservoir on its own motion, but only if pre-dissolved in part by a liquid solvent, primarily water-based solvents. Suitable liquid detergents include, but are not limited to, all kinds of liquids, including aqueous liquids, that are able to form a solution with the solid detergent product.

Suitable disinfectants include, but are not limited to, chlorine; sodium hypochlorite; bromine; iodine; iodoform; povidone iodine; benzalkonium chloride; benzethonium chloride; chlorhexidine salts, such as chlorhexidine gluconate; phenolic compounds such as cresol; hydrogen peroxide; sodium benzoate; succinic acid; sorbic acid; ascorbic acid; peracetic acid; or a mixture of any two or more such disinfectants.

The term "bleach catalyst" refers to a compound that is capable of accepting an oxygen atom from a peroxyacid and/or salt thereof, and transferring the oxygen atom to an oxidizeable substrate. A bleach catalyst may include a compound having an iminium functional group that is capable of forming an oxaziridinium functional group upon acceptance of an oxygen atom. Suitable bleach catalysts include, but are not limited to, iminium cations and polyions, iminium zwitterions, or a mixture of any two or more such catalysts. In one embodiment, the bleach catalyst includes a cyclic iminium functional group, where the cyclic moiety has a ring size of from five to eight atoms (including the nitrogen atom). In another embodiment, the bleach catalyst includes an aryliminium functional group, such as a bi-cyclic aryliminium functional group, or a 3,4-dihydroisoquinolinium functional group. Typically, the imine functional group is a quaternary imine functional group and is typically capable of forming a quaternary oxaziridinium functional group upon acceptance of an oxygen atom. Suitable iminium cations and polyions include, but are not limited to, N-methyl-3,4-dihydroisoquinolinium tetrafluoroborate and N-methyl-3,4-dihydroisoquinolinium p-toluene sulfonate. Suitable iminium zwitterions include, but are not limited to, N-(3-sulfopropyl)-3,4-dihydroisoquinolinium salts and N-[2-(sulfooxy)dodecyl]-3,4-dihydroisoquinolinium salts

The above compositions may further include a bleach catalyst represented by Formula V:

V

In Formula V, n is 0, 1, 2, 3 or 4; m is 0, 1, 2, 3, or 4; each $R^1$ is independently H, alkyl, or aryl, or any two adjacent $R^1$ groups form a fused aryl group; each $R^2$ is independently H, alkyl or a heterocyclyl group; $R^3$ is alkyl; and X is an anion.

In another aspect, a process is provided where the process includes contacting a compound represented by Formula III with a peroxymonosulfate salt to form a compound represented by Formula I:

I

III

In the above Formula I and Formula III, $R^1$ is an alkyl, alkoxy, polyalkoxy, aryl, heteroaryl, or heterocyclyl group; $R^2$ is an electron withdrawing group; and $R^1$ and $R^2$ can optionally join to form a cycloalkyl or heterocyclyl group. However, where $R^2$ is $CF_3$, $CF_2Cl$, or $CO_2R^4$, then $R^1$ is not $CH_3$ or $CF_3$. Where $R^2$ is $CO_2R^4$, $R^4$ is H, $CH_3$, $CH_2CH_2CH_3$, $CH(CH_3)_2$, or $CH_2$-β-cyclodextrin.

In certain embodiments of the process, the compound represented by Formula III is a compound represented by Formula IV, and the compound represented by Formula I is a compound represented by Formula II:

IV

II

In the above Formula IV and Formula II, $R^3$ is an electron withdrawing group; and n is 1, 2 or 3.

In the process the peroxymonosulfate salt may include, but are not limited to, those such as alkali metal peoroxymonosulfates, ammonium peroxymonosulfates, and phosphonium peroxymonosulfates. Illustrative peroxymonosulfate salts may include, but are not limited to, lithium peroxymonosulfate, sodium peroxymonosulfate, potassium peroxymonosulfate, tetramethylammonium peroxymonosulfate, tetraethylammonium peroxymonosulfate, trimethylammonium peroxymonosulfate, triethylammonium peroxymonosulfate, triisopropylammonium peroxymonosulfate, tetraisopropylammonium peroxymonosulfate, or benzyltriphenylphosphonium peroxymonosulfate. The peroxymonosulfate salt may also be a mixture of any two or more such salts. The compound of Formula I or Formula II may be provided in a buffered aqueous solution having a pH of about 7 to about 12.

Peroxymonosulfate oxidants are available commercially, for example, potassium peroxymonosulfate sold under the name OXONE® (DuPont, Wilmington Del.). Other forms of peroxymonosulfate are available with different counterions, such as alkali metal cations, alkali earth metal cations, ammonium cations, tetraalkylammonium cations, and the like. For example, a form of peroxymonosulfate having a tetrabutylammonium cation is commercially available under the name OXONE® tetrabutylammonium salt (Sigma-Aldrich, St. Louis, Mo.).

Solutions of peroxymonosulfate salt may be prepared from water and a peroxymonosulfate compound at a concentration of about 0.1 millimolar to about 1 molar, or in some examples from about 1 millimolar to about 100 millimolar. In some examples, a peroxymonosulfate solution may include a base or buffer to adjust the pH. The solution may have a pH of about 4 to about 10, or in some examples, the pH may be about 7. Suitable bases for adjusting the pH of the peroxymonosulfate solution include carbonates and bicarbonates of alkali metals and alkali earth metals, e.g., sodium bicarbonate, potassium carbonate, and the like. In some examples, a peroxymonosulfate solution may include other components which may function as processing aides, wetting aids, or the like. For example, the peroxymonosulfate solution may include organic solvents, surfactants, and/or phase transfer reagents. Suitable organic solvents include water miscible organic solvents, for example acetonitrile, alcohols, or the like. Suitable surfactants include anionic, cationic, and nonionic surfactants. Suitable phase transfer reagents include, for example, organic quaternary ammonium salts, e.g., tetrabutylammonium bromide. In some examples, the surfactant may also function as a phase transfer reagent, for example, the quaternary ammonium surfactant cetyl trimethylammonium bromide. In some examples, the peroxymonosulfate may be provided as a quaternary ammonium salt, for example, the OXONE® tetrabutylammonium salt.

In another aspect, the compound represented by Formula I or Formula II is an ionic liquid. Generally, an ionic liquid is a salt in the liquid state. Ionic liquids, especially those that are liquids at near-ambient temperature, have applications, for example, as solvents, electrically conducting fluids, oxidants, cleansers, bleaching agents, and/or decontaminants. Such ionic liquids may be suitable for use at temperatures above 25° C., and at pressures at or below 1 atm (101.325 kPa).

Methods of using any of the above described compounds and compositions are also provided. For example, a method may include cleaning an article by contacting the article with any of the compounds or compositions described above. The method may be a method of bleaching an article that includes contacting the article with any of the compounds or compositions described above. The method of use may include disinfecting an article by contacting the article with any of the compounds or compositions described above. The method of use may include decontaminating an article including the step of contacting the article with any of the compounds or compositions described above. The article may be any of a wide variety of articles. For example, in certain embodiments of the above methods, the article may be laundry, food processing equipment, surgical tools, or dishes.

In another aspect, a method of oxidizing a substrate is provided including the step of contacting the substrate with any of the compounds or compositions described above. For example, the substrate may include chemical waste, a pesticide, an herbicide, chemical warfare agent, or a biological warfare agent. Oxidation of such substrates may lead to deactivation of the toxic effects of such substrates. Illustrative chemical waste that may be deactivated by oxidation include, but are not limited to, polychlorinated biphenyls (PCBs), sulfides, alkenes, alkynes, aldehydes, pyridyl compounds, or primary amines. Illustrative pesticides may includes those substances used to control and/or eliminate pests such as an insect (e.g., a mosquito, a fly, a wasp, an ant, a woodlice, a locust, a grasshopper, etc.), a fungus, or other bugs (e.g., a spider, a centipede) or pests. Illustrative pesticides that may be deactivated by oxidation include, but are not limited to, thiamethoxam, abamectin, emamectin benzoate, spinosad, chlorpyrifos, chlorpyrifos-methyl, profenofos, lufenuron, indoxacarb, lambda-cyhalothrin, pymetrozine, pirimicarb, methidathion, imidacloprid, acetamiprid, thiacloprid, fipronil, methoxyfenozide, chlorfenapyr, pyridaben, novaluron, noviflumuron, pyridalyl, propargite or piperonyl butoxide. The above referred to herbicides includes any composition having activity against a wide variety of weeds, for use in ordinary crop lands such as plowing cultivation crop fields, non-tilled cropping fields, paddies, orchards and the like, and non-crop land such as sports grounds, vacant lands, forest lands, railroad sides and the like. Illustrative herbicides that may be deactivated by oxidation include, but are not limited to, glyphosate, pyrazosulfuron-ethyl, bensulfuron-methyl, cinosulfuron, imazosulfuron, azimsulfuron, halosulfuron-methyl, pretilachlor, esprocarb, pyrazolate, pyrazoxyfen, benzofenap, daimuron, bromobutide, naproanilide, clomeprop, CNP, chlomethoxynil, bifenox, oxadiazon, and combinations thereof.

Biological warfare agents referred to above include, but are not limited to, disease-causing bacteria, viruses, fungi, parasites, proteins, or biological toxins. For example, disease-causing bacteria include, but are not limited to, *Bacillus anthracis*, a *Brucella* species, *Burkholderia mallei*, *Burkholderia pseudomallei*, *Chlamydophila psittaci*, *Coxiella burnetii*, *Francisella tularensis*, *Rickettsia rickettsii*, a *Shigella* species, *Treponema pallidum*, *Vibrio cholerae*, or *Yersinia pestis*. Disease-causing viruses include, but are not limited to, Ebola, Machupo, Marburg, Variola, or yellow fever. Disease-causing proteins or biological toxins include, but are not limited to, staphlylococcal enterotoxin B, saxitoxin, botulinum toxin, aflatoxin, ricin, or abrin. Illustrative chemical warfare agents include, but are not limited to 3-quinuclidinyl benzilate, phosgene, phosgene oxime, nitrogen mustard, sulfur mustard, VR (N,N-diethyl-2-(methyl-(2-methylpropoxy)phosphoryl) sulfanylethanamine), VX (ethyl ({2-[bis(propan-2-yl)amino]ethyl}sulfanyl)(methyl)phosphinate), tabun (ethyl N,N-dimethylphosphoramidocyanidate), soman (3,3-dimethylbutan-2-yl methylphosphonofluoridate), sarin (propan-2-yl methylphosphonofluoridate), or cyclosarin (cyclohexyl methylphoshonofluoridate).

The substrate may be a chiral substrate. Where it is, as noted above, the oxidant may include a chiral compound of Formula I, to preferentially oxidize the stereochemical substrate.

In any of the above methods, the contact of the article or substrate may be conducted at an elevated temperature. For example, the article or substrate may be heated from about 25° C. to about 100° C.

In one illustrative example, the process includes contacting a first compound having a carbonyl group with an aqueous solution of $KHSO_5$ (potassium peroxymonosulfate) to convert the first compound to a dioxirane-containing compound. After completion, the aqueous solution that includes the dioxirane-containing compound is used directly.

The present technology, thus generally described, will be understood more readily by reference to the following Examples, which are provided by way of illustration and are not intended to be limiting of the present technology.

EXAMPLES

Example 1

Preparation of a Surfactant Dioxirane of Formula I

Approximately ten equivalents of N,N,N-trimethyl(dodecylamide) bromide in water are combined with approximately one equivalent of potassium monopersulfate and stirred at room temperature for 1 hour. The liquid is decanted from the solid residue to give an aqueous solution of approximately nine parts N,N,N-trimethyl(dodecylamide) bromide and approximately one part 1-(N,N,N-trimethyammonium) dodecyldioxirane bromide, a representative dioxirane of Formula I. Since the dioxirane is stabilized by the adjacent strongly electron-withdrawing N,N,N trimethyammonium group, the solution will be shelf stable at room temperature, in the absence of light.

Example 2

Comparison to Chlorine Bleach

Test articles similarly soiled with hydrophobic, colored organic contaminants can be prepared and comparatively washed with each of the following formulations, for identical times and temperatures: (a) pure water; (b) approximately ten equivalents of N,N,N-trimethyl(dodecylamide) bromide in water; (c) approximately ten equivalents each of N,N,N-trimethyl(dodecylamide) bromide and household bleach in water; (d) approximately ten equivalents of household bleach in water; and (e) the dioxirane product solution from Example 1 (approximately nine equivalents of N,N,N-trimethyl(dodecylamide) bromide and approximately one equivalent of 1-(N,N,N-trimethyammonium) dodecyldioxirane bromide.

Comparative washings will show that solution (a) hardly affects the soiled test article at all, while solution (d) results in some surface bleaching of the article. Solutions (b), (c), and (e) will substantially remove the hydrophobic organic contaminants from the article and disperse them in the water; solutions (c) and (e) will result in substantial oxidation of the hydrophobic organic contaminants, with solution (c) producing a significant amount of chlorinated organic compounds. Solution (e) will clean and bleach the test article without leaving toxic byproducts such as chlorinated organics. As summarized in Table 1 below, cleaning solutions based on a dioxirane of Formula I are more effective and less toxic cleaners than bleach and conventional detergents.

TABLE 1

| Solution | Cleaning effects | Bleaching effects | Toxic Byproducts produced |
|---|---|---|---|
| (a) | hardly any | trace amounts or none | trace amounts or none |
| (b) | substantially removes the hydrophobic organic contaminants from the article and disperses them in the water | trace amounts or none | trace amounts or none |
| (c) | substantially removes the hydrophobic organic contaminants from the article and disperses them in the water | substantial oxidation of the hydrophobic organic contaminant | significant amounts of chlorinated organic compounds |
| (d) | hardly any | some surface bleaching of the article | significant amounts of chlorinated organic compounds |
| (e) | substantially removes the hydrophobic organic contaminants from the article and disperses them in the water | substantial oxidation of the hydrophobic organic contaminant | trace amounts or none |

Example 3

Creation of an Ionic Liquid from a Dioxirane of Formula II, and Destruction of PCBs Approximately one equivalent of caprolactam is dissolved in benzene (approximately three times the caprolactam by weight). The solution is cooled in an ice bath, one equivalent of $HBF_4$ is added dropwise over 30 minutes, and the mixture is stirred for 4 hours at room temperature. The solution is cooled in an ice bath and slightly more than one equivalent of potassium peroxymonosulfate is added. The solution is warmed to room temperature and allowed to react for 1 hour. The resulting solution is separated from any solid residue and the benzene is removed under reduced pressure, which results in a solution of about nine equivalents of the ionic liquid caprolactam hydrotetrafluoroborate, containing about one equivalent of the corresponding dioxirane of caprolactam (1,2-dioxa-4-azaspiro[2.6]nonane) hydrotetrafluoroborate, a representative dioxirane of Formula II.

The above dioxirane ionic liquid solution containing 1,2-dioxa-4-azaspiro[2.6]nonane hydrotetrafluoroborate is combined with about 0.1 molar equivalent of mixed polychlorinated biphenyl (PCB) waste. The mixture is sealed in a pressure vessel, agitated, and heated to about 150° C. for 1 hour. The pressure vessel is cooled and the contents are analyzed to show that PCB residues are not detected in the mixture. Rather, the mixture includes the ionic liquid caprolactam hydrotetrafluoroborate, carbon dioxide, water, inorganic chlorides (mostly HCl), and some small oxygenated organic fragments. Such ionic liquids, based on a dioxirane of Formula II, are more effective at destroying PCBs than conventional ionic liquids.

Equivalents

The embodiments, illustratively described herein may suitably be practiced in the absence of any element or elements, limitation or limitations, not specifically disclosed herein. Thus, for example, the terms 'comprising,' including, 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A compound represented by Formula I or a salt thereof;

I wherein:
$R^1$ is a $C_4$-$C_{24}$ alkyl;
$R^2$ is selected from the group consisting of —$N^+R^4R^5R^6$, $NO_2$, CN, C(O)$R^7$, $CO_2R^7$, $SOR^7$, or $SO_2R^7$;
$R^4$ is H or alkyl;
$R^5$ is H or alkyl;
$R^6$ is H or alkyl;
any two of $R^4$, $R^5$, and $R^6$ can optionally join to form a heterocyclyl group;
$R^7$ is H, alkyl, polyalkoxy, aryl, heteroaryl, or heterocyclyl group; and
$R^1$ and $R^2$ can optionally join to form a cycloalkyl group.

2. The compound of claim 1, wherein $R^1$ is a $C_8$-$C_{16}$ alkyl.

3. The compound of claim 1, wherein at least one of $R^1$ and $R^2$ is a group that is chiral.

4. The compound of claim 1, wherein $R^2$ is —$N^+R^4R^5R^6$.

5. The compound of claim 4, wherein $R^4$, $R^5$, and $R^6$ are the same and are H or $C_1$-$C_{12}$ alkyl.

6. The compound of claim 4, wherein $R^4$, $R^5$, and $R^6$ are all different, and are H or $C_1$-$C_{12}$ alkyl.

7. The compound of claim 1, wherein $R^4$, $R^5$, and $R^6$ are independently H, methyl, or benzyl.

8. A compound represented by Formula II,

II wherein $R^3$ is selected from the group consisting of —$N^+R^4R^5$, —SO—, or —$SO_2$—;

$R^4$ is H or alkyl; $R^5$ is H or alkyl; or $R^4$ and $R^5$ can optionally join to form a heterocyclyl group; and
n is 1, 2 or 3.

9. The compound of claim 8, wherein n is 1.

10. The compound of claim 8, wherein $R^3$ is —$N^+R^4R^5$—.

11. The compound of claim 10, wherein $R^4$ and $R^5$ are the same and are H or $C_1$-$C_{12}$ alkyl.

12. The compound of claim 10, wherein $R^4$ and $R^5$ are different, and are H or $C_1$-$C_{12}$ alkyl.

13. The compound of claim 10, wherein the —$N^+R^4R^5$— is chiral at the nitrogen atom.

14. The compound of claim 8, wherein $R^4$ and $R^5$ are independently H, methyl, or benzyl.

15. A process comprising:
contacting a compound represented by Formula IV with a peroxymonosulfate salt to form a compound represented by Formula II:

IV and

II wherein:
$R^3$ is selected from the group consisting of —$N^{30}R^4R^5$, —SO—, or —$SO_2$—;
$R^4$ is H or alkyl; $R^5$ is H or alkyl; or $R^4$ and $R^5$ can optionally join to form a heterocyclyl group; and
n is 1, 2 or 3.

16. The process of claim 15, wherein the peroxymonosulfate salt comprises lithium peroxymonosulfate, sodium peroxymonosulfate, potassium peroxymonosulfate, tetramethylammonium peroxymonosulfate, tetraethylammonium peroxymonosulfate, trimethylammonium peroxymonosulfate, triethylammonium peroxymonosulfate, triisopropylammonium peroxymonosulfate, tetraisopropylammonium peroxymonosulfate, benzyltriphenylphosphonium peroxymonosulfate, or combinations of any two or more thereof.

17. A method of cleaning an article comprising the step of contacting the article with a compound of claim 1.

18. A method of oxidizing a substrate comprising the step of contacting the substrate with a compound of claim 1.

* * * * *

UNITED STATES PATENT AND TRADEMARK OFFICE
CERTIFICATE OF CORRECTION

Page 1 of 2

PATENT NO. : 8,916,513 B2
APPLICATION NO. : 13/554633
DATED : December 23, 2014
INVENTOR(S) : Anderson It is certified that error appears in the above-identified patent and that said Letters Patent is hereby corrected as shown below:

On the Title Page

Item (22), in Column 1, Line 1, delete "Filed: Jul. 20, 2012" and insert -- PCT Filed: Feb. 15, 2012 --, therefor.

Below Item (22), in Column 1,
insert -- (86) PCT No.: PCT/US2012/025211
§ 371(c)(1), (2), (4) Date: Jul. 20, 2012 --.

Item (56), under "OTHER PUBLICATIONS", in Column 2, Line 9, delete "Keto-derivatised" and insert -- Keto-derivatized --, therefor.

In the Specification

In Column 1, Lines 8-12, delete "This application claims the benefit of International Application Serial No. PCT/US2012/025211, filed on Feb. 15, 2012, the entire disclosure of which is hereby incorporated by reference for all purposes in its entirety as if fully set forth herein." and insert -- This application claims the benefit under 35 U.S.C. §371 of International Application Serial No. PCT/US2012/025211, filed on Feb. 15, 2012, the entire disclosure of which is hereby incorporated by reference for all purposes as if fully set forth herein. --, therefor.

In Column 11, Line 9, delete "(sulfooxy)dodecyl]-3,4-dihydroisoquinolinium salts" and insert -- (sulfoxy)dodecyl]-3,4-dihydroisoquinolinium salts. --, therefor.

In Column 11, Line 17, delete "$(R^2)_n$" and insert -- $(R^1)_n$ --, therefor.

Signed and Sealed this
Fourteenth Day of July, 2015

Michelle K. Lee
*Director of the United States Patent and Trademark Office*

CERTIFICATE OF CORRECTION (continued)

In Column 12, Lines 4-5, delete "peoroxymonosulfates," and insert -- peroxymonosulfates, --, therefor.

In Column 13, Line 57, delete "staphylococcal" and insert -- staphylococcal --, therefor.

In Column 13, Line 67, delete "methylphoshonofluoridate)." and insert -- methylphosphonofluoridate). --, therefor.

In Column 14, Line 32, delete "(N,N,N-trimethyammonium)" and insert -- (N,N,N-trimethylammonium) --, therefor.

In Column 14, Line 35, delete "trimethyammonium" and insert -- trimethylammonium --, therefor.

In Column 14, Line 54, delete "trimethyammonium)" and insert -- trimethylammonium) --, therefor.

In the Claims

In Column 18, Line 34, in Claim 15, delete "-$N^{30}$ $R^4R^5$," and insert -- -$N^+$ $R^4R^5$, --, therefor.